US012589076B2

(12) United States Patent
Laurichesse et al.

(10) Patent No.: US 12,589,076 B2
(45) Date of Patent: Mar. 31, 2026

(54) GELATIN CAPSULES WITH GROUND CALCIUM CARBONATE

(71) Applicant: CAPSUGEL BELGIUM NV, Bornem (BE)

(72) Inventors: Stephanie Laurichesse, Illkirch-Graffenstaden (FR); Ljiljana Palangetic, Colmar (FR); Stefaan Vanquickenborne, Rijmenam (BE)

(73) Assignee: Capsugel Belgium NV, Bornem (BE)

( * ) Notice: Subject to any disclaimer, the term of this patent is extended or adjusted under 35 U.S.C. 154(b) by 687 days.

(21) Appl. No.: 17/761,296

(22) PCT Filed: Oct. 8, 2020

(86) PCT No.: PCT/EP2020/078280
§ 371 (c)(1),
(2) Date: Mar. 17, 2022

(87) PCT Pub. No.: WO2021/069590
PCT Pub. Date: Apr. 15, 2021

(65) Prior Publication Data
US 2022/0347106 A1      Nov. 3, 2022

(30) Foreign Application Priority Data

| Oct. 10, 2019 | (EP) | 19202478 |
| Oct. 30, 2019 | (EP) | 19206112 |
| Nov. 15, 2019 | (EP) | 19209355 |
| May 8, 2020 | (EP) | 20173739 |

(51) Int. Cl.

| A61K 9/48 | (2006.01) |
| A61G 19/00 | (2006.01) |
| A61K 8/11 | (2006.01) |
| A61K 8/19 | (2006.01) |
| A61K 8/65 | (2006.01) |

(52) U.S. Cl.
CPC ........... *A61K 9/4816* (2013.01); *A61G 19/00* (2013.01); *A61K 8/11* (2013.01); *A61K 8/19* (2013.01); *A61K 8/65* (2013.01); *A61K 9/4825* (2013.01); *A61K 9/4833* (2013.01)

(58) Field of Classification Search
CPC .......... A61K 9/4816; A61K 8/11; A61K 8/19; A61K 8/65; A61K 9/4825; A61K 9/4833; A61K 47/02; A61Q 19/00
See application file for complete search history.

(56) References Cited

U.S. PATENT DOCUMENTS

| 3,108,995 A | * | 10/1963 | Tourtellotte | A23J 3/06 |
| | | | | 426/576 |
| 3,784,684 A | | 1/1974 | Bossert et al. | |
| 4,705,658 A | * | 11/1987 | Lukas | C09H 9/00 |
| | | | | 264/304 |
| 4,993,137 A | | 2/1991 | Muto et al. | |
| 6,071,536 A | | 6/2000 | Suzuki et al. | |
| 6,790,495 B1 | | 9/2004 | Tomka et al. | |
| 11,517,535 B2 | * | 12/2022 | Palangetic | A61K 9/4825 |
| 2005/0214361 A1 | | 9/2005 | Mizutani et al. | |
| 2009/0010975 A1 | | 1/2009 | Shiraishi | |
| 2013/0209554 A1 | * | 8/2013 | Keenan | A61K 9/4825 |
| | | | | 427/2.21 |
| 2015/0057370 A1 | * | 2/2015 | Yoneda | A61K 9/4858 |
| | | | | 514/774 |
| 2019/0105278 A1 | | 4/2019 | Watzig et al. | |
| 2020/0187538 A1 | | 6/2020 | Budde et al. | |

FOREIGN PATENT DOCUMENTS

| CA | 3 100 248 A1 | 11/2019 |
| CN | 101961346 A | 2/2011 |
| CN | 102295788 A | 12/2011 |
| CN | 105395513 A | 3/2016 |
| CN | 105796803 A | 7/2016 |
| CN | 106135153 A | 11/2016 |
| CN | 112118835 A | 12/2020 |
| EP | 3400810 A1 | 11/2018 |
| EP | 3758685 A1 | 1/2021 |
| JP | S48-028621 A | 4/1973 |
| JP | S61100516 A | 5/1986 |
| JP | H07124462 A * | 5/1995 |
| JP | H11-292791 A | 10/1999 |
| JP | 2003-300872 A | 10/2003 |
| JP | 2007284394 A | 11/2007 |
| JP | 2010-174043 A | 8/2010 |
| JP | 2013515715 A | 5/2013 |
| JP | 2019515917 A | 6/2019 |
| WO | 1996029996 A1 | 10/1996 |
| WO | WO 2001/07507 A1 | 2/2001 |
| WO | 2011080647 A2 | 7/2011 |
| WO | WO 2017/182350 A1 | 10/2017 |
| WO | WO 2019/219693 A1 | 11/2019 |

OTHER PUBLICATIONS

Tanabe et. al. JPH07124462A—machine translation (Year: 1995).*
Chen et. al. Effects of rotation speed and media density on particle size distribution and structure of ground calcium carbonate in a planetary ball mill. Advanced Powder Technology 26 (2015) 505-510 (Year: 2015).*
Basicmedical Key et. al. "Hard Capsules" 2016. (Year: 2016).*
Tanabe. JP-H07124462-A—machine translation (Year: 1995).*
Ataman "Sorbitan Laurate" 2023 (Year: 2023).*
Tanabe. JPH07124462A—machine translation provided.(Year: 1995).*
Chen "Effects of rotation speed and media density on particle size distribution and structure of ground calcium carbonate in a planetary ball mill" Advanced Powder Technology, 2015 (Year: 2015).*
Basicmedical Key "Hard Capsules" 2016 (Year: 2016).*
Shimokawa "Pharmaceutical formulation analysis of gelatin-based soft capsule film sheets using near-infrared spectroscopy" (Journal of Drug Delivery Science and Technology, 2018 (Year: 2018).*

(Continued)

*Primary Examiner* — Sean M Basquill
*Assistant Examiner* — Rajan Pragani
(74) *Attorney, Agent, or Firm* — Klarquist Sparkman, LLP

(57) ABSTRACT

The invention discloses opaque capsule shells made from gelatin with ground CaCO$_3$ as opacifier; and a method for making them.

18 Claims, No Drawings

(56) References Cited

OTHER PUBLICATIONS

Gullapalli "Soft Gelatin Capsules (Softgels)" J. of Pharm Sci, 2010 (Year: 2010).*

Office Action, dated Apr. 11, 2023, issued in related Japan Application No. 2020-564215 (w/English-language Translation). 6 pages.

Nora Hick (Authorized Officer), International Search Report and Written Opinion dated Jan. 25, 2021 for International Application No. PCT/EP2020/078280, 11 pages.

Third Party Observation dated Feb. 9, 2022 for International Application No. PCT/2020/078280, 22 pages with English translation.

Brian E Jones, "Manufacture and properties of two-piece hard capsules", Pharmaceutical Capsules, Second Edition, 2004, pp. 79-83.

Wikipedia, Differences between versions of "Calcium Carbonate", Aug. 28, 2019, https://ja.wikipedia.org/w/index.php?title=%E7%82%AD%E9%85%B8%E3%82%AB%E3%83%AB%E3%82%B7%E3%82%A6%E3%83%A0&diff=74022621&oldid=74021348, 6 pages with English translation.

Communication of a Notice of Opposition, dated May 20, 2022, issued in European Application No. 19721509.8, 26 pages.

Communication pursuant to Article 94(3) EPC, dated Aug. 29, 2022, issued in European Patent Application No. 20785767.3, 4 pages.

International Preliminary Examination Report for PCT/EP2019/062360, mailed Sep. 8, 2020.

International Search Report and Written Opinion for PCT/EP2019/062360, mailed Aug. 23, 2019.

Sato et al., "Discrimination Between Natural Calcium Carbonate and Synthetic Calcium Carbonate," Japanese Central Customs Laboratory Report, Dec. 2019, 12 pages, and English-language translation, 22 pages.

Sheskey et al., *Handbook of Pharmaceutical Excipients*, Pharmaceutical Press, 2017, pp. 138-139, 5 pages.

Brief Communication (Oral Proceedings European Patent No. 3758685B1), Jul. 28, 2023, 11 pages.

"D13: Comparative examples," submitted with Reply to Communication of a Notice of Opposition dated Sep. 26, 2022, 2 pages.

Information sheet of Cal-Carb 0 ground calcium carbonate cited in point 2 of "Handbook of Pharmaceutical Excipients," $8^{th}$ ed., 2017; excerpt, date unknown, 4 pages.

Information sheet of Cal-Carb 325 ground calcium carbonate cited in point 2 of "Handbook of Pharmaceutical Excipients," $8^{th}$ ed., 2017; excerpt, date unknown, 4 pages.

Information sheet of Calcipress™ calcium carbonate 90S cited in point 2 of "Handbook of Pharmaceutical Excipients," $8^{th}$ ed., 2017; excerpt, Particle Dynamics, Sep. 2018, 1 page.

Information sheet of DESTAB™ calcium carbonate 90SE cited in point 2 "Handbook of Pharmaceutical Excipients," $8^{th}$ ed., 2017; excerpt, Particle Dynamics, 2022, 5 pages.

Information sheet of E170 Calcium carbonate, cited in point 2 of "Handbook of Pharmaceutical Excipients," $8^{th}$ ed., 2017; excerpt, Sep. 5, 2021, 2 pages.

Information sheet of MagGran® granulates cited in point 2 of "Handbook of Pharmaceutical Excipients," $8^{th}$ ed., 2017; excerpt, Pharmaceutical Networking, Sep. 22, 2014, 8 pages.

Reply to Communication of a Notice of Opposition, (Opposition against European Patent No. EP3758685B1), Sep. 26, 2022, 12 pages.

Reply to Summons to Attend Oral Proceedings (Opposition against European Patent No. EP3758685B1), Jul. 26, 2023, 6 pages.

Safety data sheet of Precipitated Calcium Carbonate cited in point 2 of "Handbook of Pharmaceutical Excipients," $8^{th}$ ed., 2017; excerpt, Minerals Technologies, Jan. 12, 2009; Revision Date: Jul. 23, 2019, 9 pages.

Specification of Magnesia 452 calcium carbonate, Magnesia Mineral Compounds, Dec. 7, 2017, 2 pages.

Summons to Attend Oral Proceedings Pursuant to Rule 115(1) EPC, European Patent No. 3758685B1, Oct. 31, 2022, 25 pages.

* cited by examiner

GELATIN CAPSULES WITH GROUND CALCIUM CARBONATE

CROSS-REFERENCE TO RELATED APPLICATIONS

This application is a U.S. National Stage application of PCT/EP2020/078280 filed 8 Oct. 2020, which claims priority to European Patent Application No. 19202478.4 filed 10 Oct. 2019, European Patent Application 19206112.5 filed 30 Oct. 2019, European Patent Application No. 19209355.7 filed 15 Nov. 2019, and European Patent Application No. 20173739.2 filed 8 May 2020, the entire disclosures of which are hereby incorporated by reference in their entireties.

The invention discloses opaque capsule shells made from gelatin with ground $CaCO_3$ as opacifier; and a method for making them.

BACKGROUND OF THE INVENTION

Certain medicaments or other active ingredients such as nutraceutical are not light stable but are sensitive to degradation by light and need to be stored in a light-shielded manner. Within capsules, the opacity of the capsule shell hence regulates the light-shielding. Typically in the prior art, titanium dioxide is used for creating opacity in the capsule shells.

There are certain concerns about and restrictive regulations of the use of titanium dioxide as opacifier in capsule shells which necessitate the search for a replacement.

U.S. Pat. No. 6,790,495 B1 discloses the use of calcium carbonate in capsule shells based in starch. The type of calcium carbonate which use is not mentioned.

CN 105 796 803 A (embodiment 15) discloses a soft capsule shell comprising gelatin (39 wt %), ground CaCO3 (GCC) (3 wt %), methylparahydroxybenzoate (0.08 wt %), propyl parahydroxybenzoate (0.02 wt %), greyish purple (0.2 wt %) and the water of surplus.

CN 105 796 803 A is silent about capsule shells whose main component with 70 wt % or more is gelatin.

There was a need for finding a suitable replacement of titanium dioxide as opacifier in capsule shells based mainly on gelatin as wall forming polymer.

Surprisingly it was found that ground calcium carbonate GCC shows better behavior with respect to crosslinking, tensile strength and light transmittance in gelatin capsule shells than precipitated calcium carbonate PCC and encapsulated calcium carbonate ECC: GCC shows a better dissolution behavior, higher tensile strength and lower light transmittance than PCC or ECC when used as opacifier in capsule shells.

Abbreviations and Definitions Used in this Specification

ECC Encapsulated $CaCO_3$
GCC Ground $CaCO_3$
HGC hard gelatin capsule
PCC precipitated $CaCO_3$
RH relative humidity
SLS sodium lauryl sulfate
SML sorbitan mono laurate
wt % weight percent, percent by weight

SUMMARY OF THE INVENTION

Subject of the invention is a capsule shell CAPSSHELL comprising gelatin and GCC, GCC is ground $CaCO_3$, wherein CAPSSHELL comprises from 70 to 97 wt % of gelatin, with the wt % being based on the total weight of dry CAPSSHELL

DETAILED DESCRIPTION OF THE INVENTION

CAPSSHELL is a capsule shell for filling with an active pharmaceutical ingredient, medicament, nutritional supplement, nutraceutical, vitamin, mineral, cosmetic, health food or a mixture thereof.

The gelatin and the GCC are contained in the capsule shell itself, that is in the wall that actually builds the capsule shell. Another word for "build" may be "constitute" or "form". The gelatin is the film forming substance that actually builds the wall, that is that builds the capsule shell itself; the GCC is contained in the gelatin, that is the GCC is contained in the wall.

The gelatin and the GCC meant by the invention are not meant to be contained in the content which is filled into the capsule shell, such as a medicament etc.

CAPSSHELL may comprise from 3 to 12 wt %, preferably from 3.5 to 11.5 wt %, more preferably from 4 to 11 wt %, even more preferably from 4.5 to 10.5 wt %, of GCC, with the wt % being based on the total weight of dry CAPSSHELL.

In one embodiment, CAPSSHELL may comprise from 3 to 7 wt %, preferably from 3.5 to 6 wt %, more preferably from 4 to 6 wt %, even more preferably from 4.5 to 5.5 wt %, of GCC, with the wt % being based on the total weight of dry CAPSSHELL.

In another embodiment, CAPSSHELL may comprise from 8 to 12 wt %, preferably from 6 to 11.5 wt %, more preferably from 9 to 11 wt %, even more preferably from 9.5 to 10.5 wt %, of GCC, with the wt % being based on the total weight of dry CAPSSHELL.

CAPSSHELL may comprise preferably from 75 to 96.5 wt %, more preferably from 75 to 96 wt %, even more preferably from 80 to 96 wt %, especially from 80 to 95.5 wt %, in another embodiment from 85 to 96 wt %, more especially from 87.5 to 96 wt %, in another embodiment from 85 to 95.5 wt %, even more especially from 87.5 to 95.5 wt %, of gelatin, with the wt % being based on the total weight of dry CAPSSHELL.

In one embodiment, CAPSSHELL may comprise from 75 to 97 wt %, preferably from 80 to 96 wt %, more preferably from 85 to 95.5 wt %, even more preferably 90 to 95.5 wt %, of gelatin, with the wt % being based on the total weight of dry CAPSSHELL.

In another embodiment, CAPSSHELL may comprise from 70 to 92 wt %, preferably from 75 to 91 wt %, more preferably from 80 to 90.5 wt %, even more preferably 85 to 90.5 wt %, of gelatin, with the wt % being based on the total weight of dry CAPSSHELL.

The GCC may have a median particle size or a D50 of from 0.2 to 5 micrometer, preferably from 0.5 to 5 micrometer, more preferably from 1 to 5 micrometer, even more preferably from 1 to 4 micrometer.

The term "D50", indicates that in the particle mixture, the diameter of 50% (on the total mass) of the particles is smaller than, and the diameter of the other 50% (on the total mass) of the particles is larger than the indicated D50 value. Typical measurement techniques are sieve analysis, direct imaging, for examples with electron microscopy, and laser diffraction and are known in the art and are chosen by the skilled person according to the D50 which the powder which is examined is expected to have.

Preferably, GCC particles have a substantially round or prismatic particle shape. In a particular embodiment, GCC particles are uniform round or prismatic particles.

In one embodiment CAPSSHELL may have a light transmittance at 650 nm of 45% or lower, preferably of 43% or lower more preferably 42% or lower.

In one embodiment CAPSSHELL may have a light transmittance at 650 nm of 22% or lower, preferably of 21% or lower, more preferably 20% or lower.

CAPSSHELL may be a hard or soft capsule shell, preferably a hard capsule shell.

The wall thickness of CAPSSHELL is known to the skilled person, a typical value may be 100 micrometer, a typical range may be from 90 to 110 micrometer.

Typical sizes of CAPSSHELL are known to the skilled person and may be for examples expressed in the sizes 000, 00, 0, 1, 2 or 3.

CAPSSHELL may comprise water. The water stems from the production process which is using a aqueous mixture for preparing CAPSSHELL, so the water in CAPSSHELL is typically residual water remaining in CAPSSHELL after drying. Typical content of water in CAPSSHELL is 25 wt % or less, preferably 20 wt % less than, more preferably from 0 to 14 wt %, even more preferably from 1 to 14 wt %, especially from 2 to 14 wt %, more preferably from 3 to 14 wt %, of water, the wt % being based on the weight of the CAPSSHELL.

CAPSSHELL may, additionally to the gelatin and the GCC, comprise one or more additives ADD, ADD is a viscosity modifier, defoaming aid, plasticizer, lubricant, colorant, solvent, solvent aid, surfactant, dispersant, solubilizer, stabilizer, corrective, sweetener, absorbent, adsorbent, adherent's, antioxidant, antiseptic, preservative, desiccant, flavor, perfume, pH adjuster, binder, humectant, disintegrating agent, release-controlling agent, acid, salt, or a mixture therefore.

CAPSSHELL may, additionally to the gelatin and the GCC, comprise one or more additives ADD, ADD is a viscosity modifier, defoaming aid, plasticizer, colorant, surfactant, dispersant, antioxidant, pH adjuster, acid, salt, or a mixture therefore.

Colorant may be a pigment or a dye.

Plastiziser may be glycerol, sorbitol or lecithin.

Dispersant may be (iota-)carrageenan, sodium lauryl sulfate, sorbitan, or lecithin.

Antioxidant may be ascorbic acid.

pH adjuster may be a salt such as $Na_2HPO_4$ or $K_2HPO_4$.

Acid may be acetic acid or ascorbic acid.

Typical amount of acid may be from 0.025 to 0.75 wt %, preferably from 0.04 to 0.6 wt %, the wt % being based on the total weight of dry CAPSSHELL.

Possible content of ADD may be from 0.025 to 25 wt %, preferably from 0.04 to 22 wt %, the wt % being based on the total weight of dry CAPSSHELL.

Further subject of the invention is a method for preparation of CAPSSHELL, wherein CAPSSHELL is formed by a process PROCFORMCAPS for forming a capsule shell from a dispersion DIPDISP, DIPDISP is a dispersion of GCC in water comprising dissolved gelatin; with CAPSSHELL as defined herein, also with all its embodiments.

PROCFORMCAPS may be any conventional process for forming capsule shells known to the skilled person, such as extrusion moulding, injection moulding, casting or dip molding.

Dip molding can also be called dip coating.

CAPSSHELL made by dip molding comprises two halves of a capsule shell, the two halves are the called the cap and the body. Cap and body are two separate parts. When joined together they form the capsule, or the capsule shell, which can be empty or filled. The cap is form by a mold pin having the respective geometric shape complementary to the desired shape of the cap. The body is form by a mold pin having the respective geometric shape complementary to the desired shape of the body. By using the respective mold pin the dip molding either the cap or the body is obtained.

CAPSSHELL may therefore comprise two parts, the cap and the body. Said cap and body are telescopically engageable to provide CAPSSHELL. Typically, the cap and the body have each two regions, a dome shaped region, which is the closed end of the cap or of the body respectively, and an essentially cylindrically shaped region, which extends from the dome shaped region and which ends with the open end of the cap or of the body respectively.

The essentially cylindrically shaped region of the cap, or at least part of it, is telescopically engageable with the essentially cylindrically shaped region of the body, or at least with part of it. It is essentially an inserting of the body into the cap or vice versa. This inserting is typically a sliding of the cap over the body or vice versa. Typically the cap slides over the body. Thereby the essentially cylindrically shaped region of the body, or at least part of this region of the body, is inside the essentially cylindrically shaped region of the cap, or at least inside part of this region of the cap. So the essentially cylindrically regions of cap and body slide over the other one, as the case may be. So typically the body is inserted into the cap, i.e. the body slides into the cap.

Dip molding comprises the steps of:

dipping a mold pin for the first half of CAPSSHELL in DIPDISP;

allowing a film to form on the mold pin after the dipping to provide a film on the mold pin;

drying said film on the mold pin providing a half of a capsule shell; and removing the half of a capsule shell from the mold pin;

repeating the dip molding with the mold pin for the other half of CAPSSHELL;

with DIPDISP as defined herein, also with all its embodiments.

After the preparation of both halves of CAPSSHELL, both halves are joined with each other to form the capsule.

The half of a capsule shell which is removed from the mold pin may have a size which is still longer then the target length of the desired half of a capsule shell, in this case the half of the capsule shell on the mold pin and after removal from the mold pin represents a green body or can also be called an unmachined part, and is cut to the desired size to provide the desired half of a capsule shell in the desired length.

The mold pin may have an elevated temperature PINTEMP for the dip molding. In one embodiment it has the elevated temperature when it is dipped into DIPDISP and while the film is dried on the mold pin after the dipping.

PINTEMP may be from ambient temperature to 40° C., preferably from ambient temperature to 30° C.

The temperature of DIPDISP during the dipping of the mold pins into DIPDISP may be from ambient temperature to 75° C., preferably from 25 to 70° C., more preferably from 30 to 75° C., even more preferably from 35 to 70° C., especially from 35 to 65° C.

Drying of the film on the mold pin may be done by air drying. Drying may be done at elevated temperature The temperature for drying of the film on the mold pin may be from ambient temperature to 40° C., preferably from 20 to 35° C., more preferably from 20 to 30° C.

After the joining of both halves to form the capsule, CAPSSHELL may be further dried; this drying may be done at a temperature of from ambient temperature to 40° C., preferably from 20 to 35° C., more preferably from 20 to 30° C.

DIPDISP comprises GCC and gelatin in an amount based on the dry weight of DIPDISP which are equal to the amount of GCC and gelatin in CAPSSHELL based on the dry weight of CAPSSHELL as defined herein.

DIPDISP may be prepared by a mixing MIX of a dispersion GCCDISP of GCC in water with a solution GELSOL of gelatin in water.

GCCDISP may comprise from 20 to 35 wt %, preferably from 25 to 30 wt %, of GCC, the wt % being based on the total weight of GCCDISP.

GELSOL may comprise from 20 to 40 wt %, preferably from 25 to 35 wt %, of gelatin, the wt % being based on the total weight of GELSOL.

MIX may be done in one or more steps.

In one embodiment MIX is done in two mixing steps MIX1 and MIX2;

in MIX1 GCCDIPS is mixed with GELSOL providing a mixture MIXTUREGCCDISPGELSOL;

in MIX2 MIXTUREGCCDISPGELSOL is mixed with GELSOL to provide DIPDISP.

MIXTUREGCCDISPGELSOL may comprise from 10 to 30 wt %, preferably from 15 to 25 wt %, of gelatin, the wt % being based on the total weight of MIXTUREGCCDISPGELSOL.

MIXTUREGCCDISPGELSOL may comprise from 2 to 10 wt %, preferably from 3 to 9 wt %, more preferably from 4 to 8 wt %, of GCC, the wt % being based on the total weight of MIXTUREGCCDISPGELSOL.

The amounts of GELSOL, GCCDISP and MIXTUREGCCDISPGELSOL and their concentration and amounts of gelatin and of GCC are calculated and chosen in such a way that the desired amounts of GCC and of gelatin in DIPDISP is provided in order to provide for the desired amounts of GCC and of gelatin in CAPSSHELL.

The amounts of GCC, of gelatin and of any ADD in dry DIPDIPS is equal to the respective amounts in dry CAPSSHELL.

DIPDISP may comprise, additionally to GCC and gelatin, ADD;

with ADD as defined herein, also with all its embodiments.

DIPDISP may comprise ADD in an amount based on the dry weight of DIPDISP which are equal to the amount of any ADD in CAPSSHELL based on the dry weight of CAPSSHELL as defined herein.

GCCDISP may be prepared by a mixing MIXGCC of GCC with water.

Any mixing such as MIXGCC, MIX, MIX1 and MIX2 is preferably done under conditions of eleveated shear.

Any such mixing may be done with an Ultra Turrax from IKA-Werke GmbH & CO. KG, 79219 Staufen, Germany, or a similar instrument.

Mixing speeds may be from 5,000 to 25,000 rpm, preferably 6,000 to 23,000 rpm.

Mixing times may be from 1 to 30 min, preferably from 2 to 20 min, even more preferably from 2 to 10 min.

Conditions of elevated shear may also be referred to as high shear conditions.

MIXGCC may be done with mixing speeds of from 15,000 to 25,000 rpm, preferably 17,000 to 23,000 rpm.

Mixing times for MIXGCC may be from 4 to 30 min, preferably from 4 to 20 min, even more preferably from 4 to 10 min.

DIPDISP, GCCDISP and MIXTUREGCCDISPGELSOL have the form of a dispersion or slurry. The dispersion or the slurry is a dispersion of GCC in aqueous medium.

GELSOL may be prepared by dissolving DISSGEL of gelatin in water. DISSGEL may be done at elevated temperature, the temperature for DISSGEL may be from 35 to 100° C., preferably from 40 to 95° C.

GELSOL may be stored and used for MIX at elevated temperatures, such as from 35 to 60° C., preferably from 40 to 55° C.

Further subject of the invention is CAPSSHELL filled with a formulation FILLFORM comprising an active ingredient ACTINGR, ACTINGR may be an active pharmaceutical ingredient (API), medicament, nutritional supplement, nutraceutical, vitamin, mineral, cosmetic, health food or a mixture thereof;

with CAPSSHELL as defined herein, also with all its embodiments.

ACTINGR may be an active ingredient which is not stable in or sensible to visible or UV light, preferably visible light.

Further subject of the invention is the use of CAPSSHELL for filling with FILLFORM, with CAPSSHELL and FILLFORM as defined herein, also with all its embodiments.

FILLFORM may comprise ACTINGR in an amount from 0.05 to 100 wt %, preferably from 0.5 to 90 wt %, more preferably from 1 to 50 wt %, even more preferably from 5 to 30 wt %, the wt % being based on the total dry weight of FILLFORM.

The GCC of CAPSSHELL provides for a shielding of the ACTINGR against light.

Examples for medicaments or for API which are candidate for ACTINGR to be filled in CASPSSHELL to obtain effective light shielding are dihydropyridine derivatives (e.g., nifedipine), antiviral HIV protease inhibitors (e.g., Ritonavir, Saquinavir), therapeutic agents for hyperlipidemia (e.g., clofibrate), iodine compounds (e.g., sodium iopodate, sodium iodide), polyunsaturated fatty acid derivatives (e.g., ethyl eicosapentaenoic acid (EPA), docosahexaenoic acid (DHA)), carotenoids (e.g., lycopene, bixin, β-carotene, xanthophyll, lutein), ubiquinones (coenzyme Q) (e.g., ubidecarenone used as a metabolizable cardiac stimulant), various vitamin derivatives, as well as indomethacin, colchicine, diazepam, syrosingopine, norethisterone, piretanide, propericyazine, perphenazine, mequitazine, medazepam, menatetrenone, indenolol hydrochloride, reserpine, sofalcone, bromocriptine mesilate, bufetolol hydrochloride and oxprenolol hydrochloride when they are filled into the capsule formulation of the present invention. Among vitamin derivatives, fatsoluble ones are preferred for use. Examples include vitamin A derivatives (e.g., tretinoin, liver oil, retinol palmitate), vitamin A analogs (e.g., etretinate), vitamin D derivatives, vitamin E derivatives (e.g., tocopherol nicotinate, tocopherol acetate, tocopherol calcium succinate), or vitamin K derivatives (e.g., phytonadione (vitamin K1), menaquinone (vitamin K2), menadione (vitamin K3), menatetrenone, phytonadione).

A medicament or an API as ACTINGR can be filled into CAPSSHELL either alone or in combination with any base or carrier, additive, or excipient. Any type of base or carrier, either fat-soluble or water-soluble, can be used as long as it does not impair the medicament's or API's activity and does not affect various physical properties of CAPSSHELL, such as strength, gas permeability, and disintegration or dissolution profiles. Likewise, the base per se may be in a liquid or solid state at normal temperature as long as it can be filled into CAPSSHELL with the help of heating or dilution with other solvents, etc. Examples of such a base include vegetable oils (e.g., soybean oil, sesame oil, cottonseed oil, olive oil), fatty acid glycerides (e.g., medium chain triglycerides), propylene glycol, propylene glycol fatty acid esters, polyethylene glycol, polyvinylpyrrolidone, triacetin, liquid paraffin, polyoxyethylene sorbitan fatty acid esters, sucrose fatty acid esters, ethanol and purified water, which may be used alone or in combination. Bases preferred for dissolving fat-soluble medicaments or APIs such as vitamins A, D, E and K are vegetable oils or fatty acid glycerides, with medium chain triglycerides being particularly preferred. In the case of using a water-soluble base, it is preferable to provide a protection layer between the capsule shell layer and the medicament or API layer or a crystallization inhibitor in consideration of influences on CAPSSHELL.

A medicament or API to be filled into CAPSSHELL of the present invention is preferably exemplified by, but not limited to, those in a liquid form or those dissolved, suspended or emulsified in such a base as listed above. The medicament or API may also be in a solid form (e.g., powders, granules) or in a semi-solid form (e.g., creams or gels).

EXAMPLES

Materials and Apparatus

PCC-A Vicality Albafil, Specialty Minerals Inc., Bethlehem, PA 18017, US Precipitated Calcium Carbonate (PCC) with Particle Size, median, microns 0.7, Surface Area, m²/g 7.0, Oil Absorption, grams oil/100 grams 32

PCC-B Calopake 5970—Specialty Minerals Inc., Bethlehem, PA 18017, US Precipitated Calcium Carbonate (PCC) with Mean Particle Size microns 2.0, Surface Area, m²/g 8, GCC-1 Magnesia 452—Magnesia GmbH, 21337 Lüneburg, Germany Ground Calcium Carbonate (GCC), Particle size D50 1.5 to 2.5 micrometer GCC 2 Calcipur 110-KP, Omya International AG, 4665 Oftringen, Switzerland Ground Calcium Carbonate (GCC), Particles smaller than 2 micrometer: 38 to 52%

GCC 3 Hubercal 950 Elite, Omya International AG, 4665 Oftringen, Switzerland Ground Calcium Carbonate, Median Particle Size microns 3.6

ECC-I Capcolors White 100 WSS-P, Chr. Hansen Holding A/S, 2970 Hoersholm, Denmark Encapsulated Calcium Carbonate with calc. value 80 to 84% gelatin Porcine Skin Gelatine A240, Gel strength (Bloom) Ph. Eur./USP-NF (corr. 11, 5%) 240-336 g, GELIT A Sweden AB, Klippan Sweden UV spectrophotometer UVKON XL, tresser instruments, 64380 Rossdorf, Germany

Example 1: Preparation of HGC Melt (DIPDISP by MIX)

Step 1: Preparation of Aqueous Gelatin Solution (GELSOL by DISSGEL):

List of Compounds to Prepare Aqueous Gelatin Solution:
Dry gelatin: 32.0240 wt %
Hot water (70 to 80° C.) 41.3162 wt %

Cold water (15 to 25° C.) 26.5116 wt %

SLS 0.0224 wt %

SML 0.0261 wt %

Acetic Acid 0.0997 wt %

Preparation of Aqueous Gelatin Solution (GELSOL BY DISSGEL):

SML is mixed with hot water and dry gelatin is then added. The mixture is heated to 90° C. in 90 min. Cold water and acetic acid are then added to the mixture. Then SLS is added. The temperature of the mixture is maintained at 53° C. under stirring and vacuum 0.6 mbar for 80 min. Stirring is then stopped and the obtained aqueous solution of gelatin is kept without stirring for 80 min at 53° C. Then the gelatin aqueous solution is kept at and used with 45° C.

Step 2: Preparation of Dispersion of CaCO₃ (GCCDISP by GCCDISP):

Water was added to CaCO₃ and the mixture was homogenized with high shear mixing at 21000 rpm with an Ultra Turrax (3 times 2 minutes with 30 sec pause between each mixing) to provide a dispersion of CaCO₃ in water.

Step 3: Preparation of Slurry (MIXTUREGCCDISPGEL-SOL by MIX1):

Then aqueous gelatin solution is added and mixed into the dispersion of CaCO₃ under stirring with Ultra Turrax at 7,000 rpm during 3 min, thereby forming a slurry.

Step 4: Preparation of the HGC Melt (DIPDIPS by MIX2) with Desired Concentration of CaCO₃:

The slurry is then mixed with aqueous gelatin solution, thereby providing a HGC melt with the desired content of CaCO₃ and of gelatin by manual mixing with a respective spatula.

This procedure is used for GCC, PCC and ECC.

Table 1 shows the amounts used in each step.

TABLE 1

| Step 1 | Preparation of aqueous gelatin solution | | |
|---|---|---|---|
| | gelatin | 322.94 g | 322.94 g |
| | water | 718.79 g | 718.79 g |
| | content of gelatin | 31 wt % | 31 wt % |
| Step 2 | Preparation of Dispersion of CaCO₃ | | |
| | CaCO₃ | 22.45 g | 22.45 g |
| | water | 60 g | 60 g |
| | content of CaCO₃ | 27.2 wt % | 27.2 wt % |
| Step 3 | Preparation of slurry | | |
| | Dispersion from Step 2 | 82.45 g | 82.45 g |
| | aqueous gelatin solution from Step 1 | 20 g | 20 g |
| | CaCO₃ content | 21.9 wt % | 21.9 wt % |
| | gelatin content | 6.1 wt % | 6.1 wt % |
| Step 4 | Preparation of the HGC melt with desired concentration of CaCO₃ | | |
| | Slurry from Step 3 | 77.35 g | 81.13 g |
| | aqueous gelatin solution from Step 1 | 1021.73 g | 500 g |
| | Amount of CaCO₃ | 16.95 g | 17.8 g |
| | CaCO₃ content | 1.5 wt % based on weight of HGC melt 5 wt % based on total dry weight | 3.1 wt % based on weight of HGC melt 10 wt % based on total dry weight |
| | gelatin content | 29.4 wt % based on weight of HGC melt 95 wt % based on total dry weight | 27.5 wt % based on weight of HGC melt 90 wt % based on total dry weight |

Example 2: Forming of Films

Films were formed as follows:

Glass plates were kept at 60° C., the HGC melt with the desired content of $CaCO_3$ was kept at 55° C. and films were casted using a plate coater (CAMAG, 4132 Muttenz, Switzerland). The films were then left to dry overnight at 22° C. at a RH of 50%. Thickness of the films was between 85 and 100 micrometer.

Example 3: Testing of Films—Transmittance

Transmittance at 650 nm were tested and the results are given in Table 3.

The measurement was done with a UV spectrophotometer.

TABLE 3

| Component | Transmittance at 650 nm [%] |
|---|---|
| 5% PCC-A | 49.2 |
| 5% PCC-B | 50.00 |
| 5% ECC-I | 48.5 |
| 5% GCC-1 | 36.3 |
| 5% GCC-2 | 40.2 |
| 5% GCC-3 | 39 |
| 10% PCC-A | 27.5 |
| 10% PCC-B | 25.7 |
| 10% ECC-I | 28.8 |
| 10% GCC-1 | 19.3 |
| 10% GCC-2 | 19.3 |
| 10% GCC-3 | 19.8 |

The lower the transmittance the better, obviously GCC shows lower transmittance than PCC and than ECC

Example 4: Testing of Films—Tensile Test

Tensile tests have been performed on the films. For each sample, 20 film strips (dimensions: width 12.7 mm, length 80 mm) per $CaCO_3$ grade and percentage were cut and stored for 5 days at two different RH (23% RH and 50% RH).

Then they were tested and average values of the 20 films were calculated.

Test conditions: initial length 25 mm, speed rate 50 mm per min

Tables 4 and 5 show the results.

TABLE 4

| | Tensile test at 50% RH | |
|---|---|---|
| | Deformation [% ± std] | Deformation [Max %] |
| 5% PCC-A | 15.9 ± 6.7 | 30.4 |
| 5% PCC-B | 12.1 ± 3.4 | 21.1 |
| 5% ECC-I | 11.8 ± 5 | 24.6 |
| 5% GCC-1 | 25.2 ± 8.5 | 39.1 |
| 5% GCC-2 | 22.7 ± 12.4 | 43.6 |
| 5% GCC-3 | 23.6 ± 11.1 | 44.9 |
| 10% PCC-A | 13.3 ± 4.5 | 21.4 |
| 10% PCC-B | 11.7 ± 3.2 | 18.4 |
| 10% ECC-I | 11.5 ± 2.1 | 15.1 |
| 10% GCC-1 | 37 ± 14 | 61.1 |

TABLE 5

| | Tensile test at 23% RH | |
|---|---|---|
| | Deformation [% ± std] | Deformation [Max %] |
| 5% PCC-A | 14.8 ± 5.9 | 27.4 |
| 5% PCC-B | 18.3 ± 5 | 27.6 |
| 5% ECC-I | 12.8 ± 5.8 | 28.6 |
| 5% GCC-1 | 34.6 ± 13.5 | 55.6 |
| 5% GCC-2 | 33.4 ± 12.3 | 59.8 |
| 5% GCC-3 | 26 ± 7.2 | 39.4 |
| 10% PCC-A | 12.9 ± 6.3 | 28.8 |
| 10% PCC-B | 19.5 ± 5.2 | 28.4 |
| 10% ECC-I | 14.86 ± 6.1 | 27.4 |
| 10% GCC-1 | 42.5 ± 12 | 57.2 |

The higher the deformation the better; GCC shows highest deformation compared to PCC and to ECC.

Example 5: Dissolution Tests

The films were cut to pieces of ca. 2.5 times 3.0 cm while the weight was adjusted to a weight of 75 mg+/−1 mg.

With these film pieces first dissolution tests were performed (T=0).

Other film pieces stored in accelerated conditions (climatic chamber at 50° C.+/−2° C. and with a RH of 80+/−5% for 4 weeks) and tested after the first (T=1W), the second (T=2W) and the fourth (T=4W) week.

For testing the film pieces were placed in cage shaped sinker in a stirred dissolution media, the dissolution media used was demineralized water at 36.5 to 37.5° C.

Measurements of Optical Density (OD) were performed with UV-visible spectrophotometer at the wavelength of 218 nm. Measurements were done at the times t=0, 3, 6, 9, 12, 15 min. After these 15 min, stirring was applied to facilitate complete dissolution and then after another 15 min complete dissolution of the gelatin was obtained and measured, providing the infinity dissolution value $DO_{100\%}$.

Calculation was done by comparison with infinity dissolution value:

$$\% \text{ dissolved} = \frac{DOt - DO_0}{DO_{100\%} - DO_0} \times 100$$

with

DO optical density t time in min

Results are shown in Table 6.

TABLE 6

| | % Dissolved | | | |
|---|---|---|---|---|
| | T = 0 | T = 1 W | T = 2 W | T = 4 W |
| 5% PCC-A | 79.8 | 85.8 | 82.7 | 26.6 |
| 5% PCC-B | 94.3 | 81.1 | 69.5 | 13.2 |
| 5% GCC-1 | 84.8 | 89.6 | 91.9 | 78.9 |
| 10% GCC-1 | 84.0 | 88.8 | 87.6 | 89.1 |
| 5% GCC-2 | 91.8 | 95.9 | 83.7 | 85.8 |
| 5% GCC-3 | 95.1 | 76.9 | 87.8 | 90.7 |

In order to meet specification and thereby to qualify, the % dissolved need to be greater than 50% after 9 min of testing.

The use of PCC causes gelatin crosslinking in accelerated conditions which diminishes the dissolution ability whereas the use of ground $CaCO_3$ shows improved behavior, that is less crosslinking.

Example 6: Preparation of HGC Shell

The HGC melts prepared according to example 1 were used to produce HGC shells with capsule size 0 and standard target weights (Body 60+/−2 mg, Cap 36+/−1.2 mg) through conventional mold dipping by dipping stainless steel mold pins at room temperature (22° C.) into a the HCG melt with 45° C. A film was formed on the mold pins. After first drying of the film on the mold pins at 25 to 29° C. and 40% RH for 30 to 40 min, and a second drying at 20 to 22° C. and 50% RH for 10 min, HGC shells in form of its halves (bodies and caps) were obtained with shell wall thickness of:

top of the caps and body 120 micrometer or above
shoulder of the cap and body 80 micrometer or above
side wall thickness 100+/−20 micrometer

The invention claimed is:

1. A capsule shell comprising gelatin, a first dispersant, a second dispersant that is different from the first dispersant, and ground $CaCO_3$, wherein sodium lauryl sulfate is the first dispersant, and wherein the capsule shell comprises from 70 to 97 wt % of gelatin, with the wt % being based on the total weight of dry capsule shell;

wherein the second dispersant is sorbitan mono laurate; and wherein the capsule shell optionally further comprises a plasticizer selected from glycerol or lecithin; and wherein the capsule shell optionally further comprises water.

2. The capsule shell according to claim 1, comprising from 3 to 12 wt %, of the ground $CaCO_3$, with the wt % being based on the total weight of the dry capsule shell.

3. The capsule shell according to claim 1, comprising from 75 to 96.5 wt %, of the gelatin, with the wt % being based on the total weight of the dry capsule shell.

4. The capsule shell according to claim 1, wherein the ground $CaCO_3$ has a median particle size or a D50 of from 0.2 to 5 micrometer.

5. The capsule shell according to claim 1, wherein the capsule shell is a hard capsule shell.

6. The capsule shell according to claim 1, wherein the capsule shell comprises water.

7. The capsule shell according to claim 1, further comprising a viscosity modifier, defoaming aid, lubricant, colorant, solvent, solvent aid, surfactant, additional dispersant that is different from the first and second dispersants, solubilizer, stabilizer, corrective, sweetener, absorbent, adsorbent, adherent's, antioxidant, antiseptic, preservative, desiccant, flavor, perfume, pH adjuster, binder, humectant, disintegrating agent, release-controlling agent, acid, salt, or a mixture therefore, wherein the additional dispersant is (iota-)carrageenan, sorbitan, or lecithin.

8. The capsule shell according to claim 7, wherein the colorant is a pigment or a dye.

9. The capsule shell according to claim 1, wherein the capsule shell comprises the plasticizer.

10. The capsule shell according to claim 7, wherein the pH adjuster is $Na_2HPO_4$ or $K_2HPO_4$.

11. The capsule shell according to claim 7, wherein the acid is acetic acid or ascorbic acid.

12. A method for preparing a capsule shell according to claim 1, wherein the capsule shell is formed from a dispersion of the ground $CaCO_3$ in an aqueous solution comprising the gelatin, the sodium lauryl sulfate and sorbitan mono laurate.

13. The method according to claim 12, wherein the capsule shell is formed using extrusion moulding, injection moulding, casting or dip molding.

14. The method according to claim 13, wherein the capsule shell is made by dip molding and comprises a first half shell and a second half shell;

wherein the dip molding comprises the steps of:

dipping a mold pin in the dispersion to form a film on the mold pin;

drying the film on the mold pin to provide the first half shell;

removing the first half shell from the mold pin; and repeating the dip molding with the mold pin in the dispersion to form the second half shell.

15. The method according to claim 14, further comprising joining the first half shell and the second half shell to each other to form the capsule shell.

16. The method according to claim 12, wherein the dispersion further comprises a viscosity modifier, defoaming aid, plasticizer, lubricant, colorant, solvent, solvent aid, surfactant, additional dispersant that is different from sodium lauryl sulfate and sorbitan mono laurate, solubilizer, stabilizer, corrective, sweetener, absorbent, adsorbent, adherent's, antioxidant, antiseptic, preservative, desiccant, flavor, perfume, pH adjuster, binder, humectant, disintegrating agent, release-controlling agent, acid, salt, or a mixture therefore.

17. A capsule, comprising:

the capsule shell of claim 1; and a formulation contained within the capsule shell, the formulation comprising an active pharmaceutical ingredient, medicament, nutritional supplement, nutraceutical, vitamin, mineral, cosmetic, health food or a mixture thereof.

18. A capsule shell consisting of:

gelatin;

sodium lauryl sulfate;

sorbitan mono laurate; and ground $CaCO_3$; and optionally a plasticizer selected from glycerol or lecithin; and optionally a pH adjuster;

optionally an acid; and optionally water;

wherein the capsule shell contains from 70 to 97 wt % of gelatin, with the wt % being based on the total weight of dry capsule shell.

* * * * *